United States Patent [19]

Grunbaum

[11] 4,130,471
[45] Dec. 19, 1978

[54] MICROELECTROPHORETIC APPARATUS AND PROCESS

[76] Inventors: Robert A. Frosch, Administrator of the National Aeronautics and Space Administration, with respect to an invention of Benjamin W. Grunbaum, Moraga, Calif.

[21] Appl. No.: 850,507

[22] Filed: Nov. 10, 1977

[51] Int. Cl.² .............................................. G01N 27/26
[52] U.S. Cl. ............................. 204/180 G; 204/180 S; 204/299 R; 23/230 B; 424/12
[58] Field of Search ............... 204/180 G, 180 S, 799; 23/230 B; 424/12

[56] References Cited

U.S. PATENT DOCUMENTS

| | | | |
|---|---|---|---|
| 2,147,458 | 2/1939 | Rohland | 204/180 S X |
| 3,482,943 | 12/1969 | Csizmas et al. | 204/180 S X |
| 3,888,759 | 6/1975 | Elson et al. | 204/299 |
| 4,018,662 | 4/1977 | Ruhenstroth-Bauer | 204/180 G X |

Primary Examiner—Arthur C. Prescott
Attorney, Agent, or Firm—Darrell G. Brekke; John R. Manning; Armand McMillan

[57] ABSTRACT

New gel tray and lid assemblies designed for use in conjunction with slotted electrophoretic membranes have been developed to take advantage of recently improved microelectrophoretic accessories which include a multisample applicator capable of applying up to 10 samples consecutively or simultaneously, and a temperature control plate for dissipating the heat produced by electrophoresis in a gel. The trays and membranes can be marketed ready for use as electrophoretic media or impregnated with various specific substrates and dyes which can develop the electrophoretic patterns of up to 30 individual protein samples in up to 10 tray or membrane compartments. In addition to greatly simplifying and speeding up electrophoresis, these new methods and equipment will contribute to the standardization of processes for clinical, forensic and anthropological diagnosis and identification.

14 Claims, 38 Drawing Figures

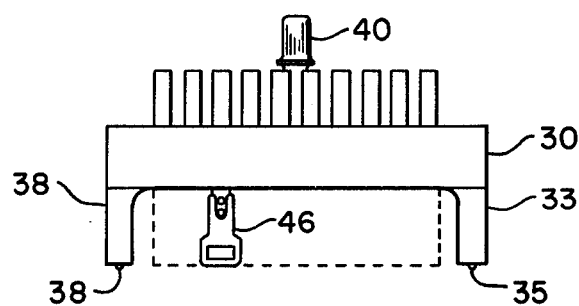
Fig-1F
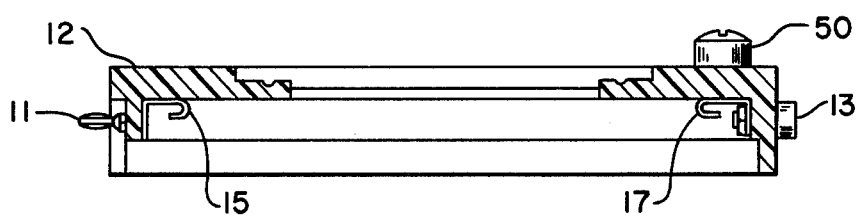
Fig-1E
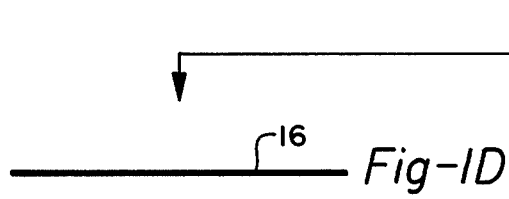
Fig-1D
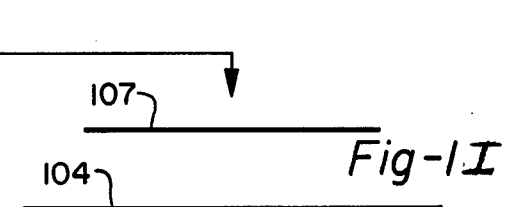
Fig-1I
Fig-1H
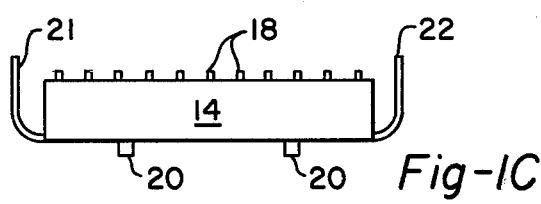
Fig-1C
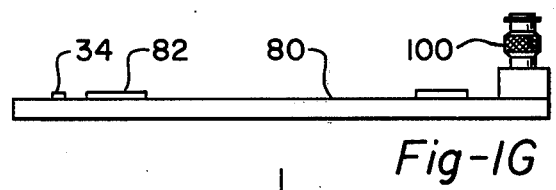
Fig-1G
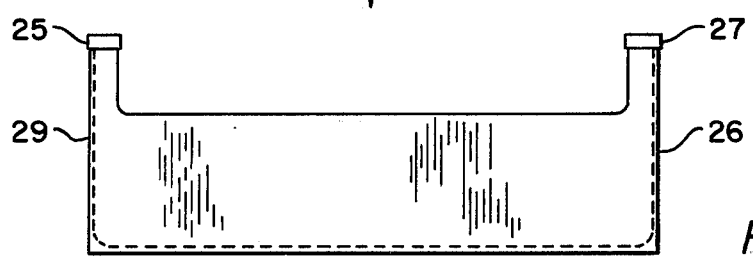
Fig-1B
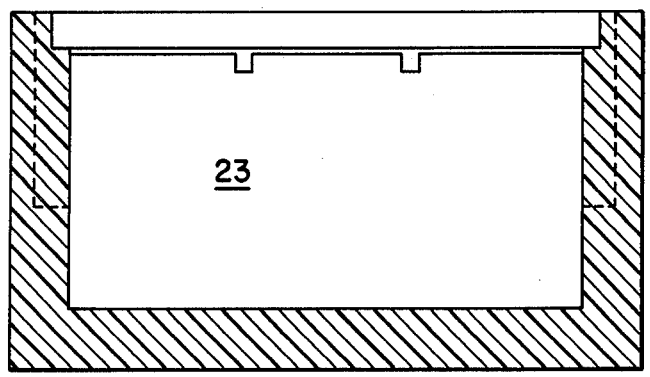
Fig-1A

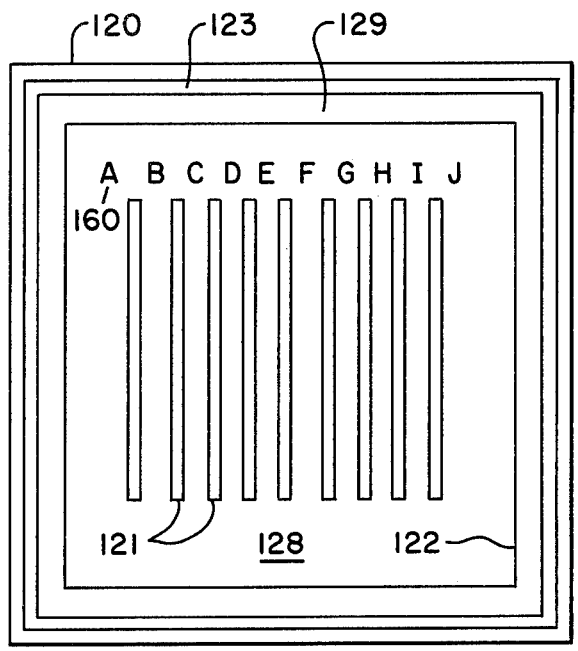
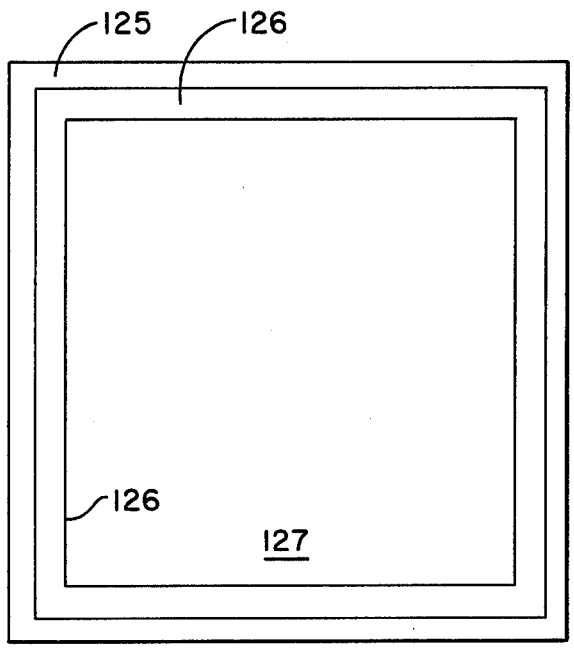
Fig-7                     Fig-9
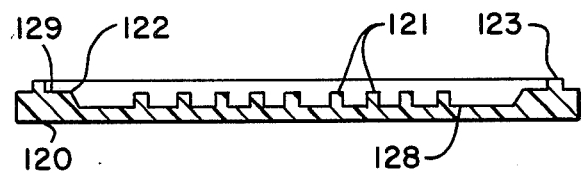
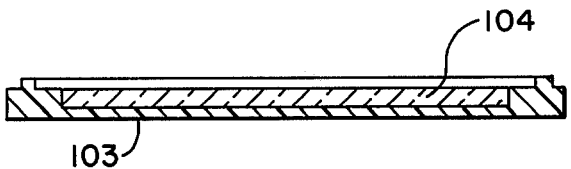
Fig-7A                    Fig-8
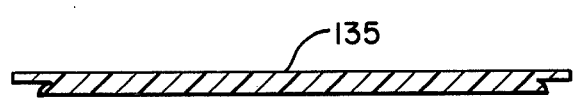
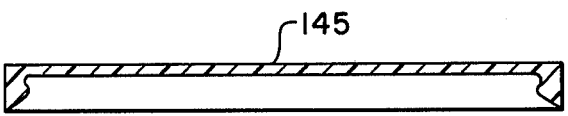
Fig-11                    Fig-13
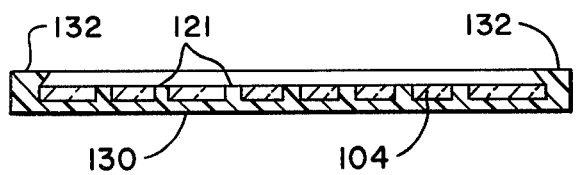
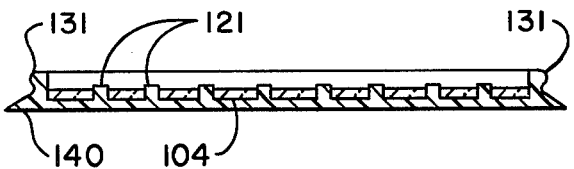
Fig-10                    Fig-12

MICROELECTROPHORETIC APPARATUS AND PROCESS

ORIGIN

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The invention relates to electrophoresis and, more particularly, to new gel trays and membranes pre-impregnated with developing reagents, which can be used in carrying out new clinical and medico-legal processes that have been rendered practical by recently developed microelectrophoretic equipment.

2. The Prior Art

In a copending patent application by the present inventor, Ser. No. 744,574, filed on Nov. 24, 1976, now U.S. Pat. No. 4,061,561 there are disclosed several improvements of microelectrophoretic apparatus which greatly simplify and standardize the microelectrophoretic process and which include: (a) designs that allow the use of either a membrane or a tray with the same basic apparatus; (b) designs which allow the two-dimensional resolution of a protein sample placed on a gel-filled tray, (c) a sample applicator and accessory equipment which permit the simultaneous and precise positioning of e.g., 10 samples.

This apparatus can be used advantageously with various conventional devices and techniques which include comartmentalized gel trays, as disclosed by Siebert et al. in U.S. Pat. No. 3,616,387 (FIG. 5 and column 3, lines 53 to 55) and slotted membranes, as disclosed by Zec in U.S. Pat. No. 3,317,418 (FIG. 7). Also, when used in conjunction with the further refined articles that are disclosed in the present application, it makes available to research scientists and laboratory technicians new and improved methodology for separation of specific proteins from microliter quantities of blood. These specific proteins are then identified through use of immunologic techniques or, more commonly, through use of indicator dyes which chemically unite with one specific type of protein and no other. These dyes make contact with the electrophoresed samples by means of an overlay, eithr cellulose acetate membrane upon gel, or gel upon cellulose acetate membrane. The overlays have been pre-impregnated with the appropriate specific substrate so that a permanent visual record of the pattern is produced on the cellulose acetate membrane, whether the membrane is serving as the supporting medium or as the overlay. This technique is described by Grunbaum in "An Automatic One-to-Eight Sample Applicator for Fast Qualitative and Quantitative Microelectrophoresis of Plasma Proteins . . . ," Microchem. J. 20, 495–510 (1975).

This apparatus is useful in research and application in the fields of Medicine, Immunology, Genetics, Biochemistry, and Forensic Science. Electrophoretic procedures which greatly increase in utility with this apparatus include determinations of significant polymorphic enzyme systems such as lactic acid dehydrogenase (LDH), alkaline phosphatase (AP), and creatine phosphokinase (CPK). It can be used for diagnostic purposes through determination of specific antibodies or antigens in the blood. In the forensic laboratory, it can be used in the phenotyping of genetic variants of enzymes and other proteins in blood for the purose of identification or individualization.

A partial list of the factors in blood that can be determined using this apparatus include the following:
lactic acid dehydrogenase (LDH)
alkaline phosphatase (AP)
creatine phosphokinase (CPK)
erythrocyte acid phosphatase (EAP)
glucose-6-phosphate dehydrogenase (G-6PD)
adenylate kinase (AK)
hemoglobin (Hb)
haptoglobin (Hp)
group specific component (Gc)
lipoprotein (Lp)
adenosine deaminase (ADA)
6-phosphogluconate dehydrogenase (6-PGD)
Glyoxylase I (GLO-I)
glutamic pyruvic transaminase (GPT)
esterase D (EsD)
Glutathione reductese (GsR)
Immunoglobulins (Ig)

Methodology for the phenotyping of additional systems is being developed.

SUMMARY OF THE INVENTION

It is an object of the invention to disclose techniques that can simplify processes of clinical diagnosis, phenotyping, and forensic identification that are based on microelectrophoreses so that such processes can be used widely and acccurately by clinical and medio-legal laboratory technicians. Another object is to provide improved accessories which render these techniques practical.

These and other objects which shall become evident in the course of the detailed description of the invention have been accomplished by providing specialized gel tray and cover assemblies containing suitable gels for electrophoresis and, in separate embodiments, one or more specific substrates for the visualization of electrophoresed proteins. Said trays are preferably divided into several compartments by parallel ribs rising from their flat bottom surface for use in simultaneous analysis of several parameters.

Also provided for these purposes are slotted membranes pre-impregnated with specific substrates for the visualization of proteins electrophoresed on the gel trays just mentioned. These membranes may be provided with an underlying coat of tough polyester and thus constitute, after use, a permanent storable electrophoretogram.

The trays and membranes described have been designed for use with recently developed improved electrophoretic apparatus disclosed in co-pending patent application Ser. No. 744,574, filed on Nov. 24, 1976, now U.S. Pat. No. 4,061,561. That patent is hereby incorporated into the present disclosure by reference. As shall be seen from some of the drawings and text hereinafter included to described that improved equipment in its aspects that relate to the present invention, its most relevant features include: (1) an applicator that can precisely and, if desired, simultaneously position up to ten samples in a membrane or a gel, without need to provide preformed depressions on the gel for receiving the samples, (2) a geometry such that either a membrane or a gel tray can be used with the same basic apparatus, and (3) a square gel tray which can be rotated 90° with respect to the electrodes so that the electrophoretic separation can ultimately be done two-dimensionally.

By means of such equipment, therefore it is now possible, inter alia, to accurately and rapidly carry out simultaneous electrophoretic separations of several polymorphic protein systems of different origin or of different nature, either on a gel or on a membrane, and to develop visual records of the patterns produced by contacting the electrophoresed samples with either a membrane or a gel, as the situation requires, said membrane or gel having been pre-impregnated with suitable specific substrate for rendering the electrophoresed protein systems visible.

The availability of the new prepackaged gels and membranes, both for electrophoresis and, when pre-impregnated with specific substrates, for developing the electrophoresed proteins, will allow a great degree of standardization between widely separated laboratories. Such an improvement in the art, while being certainly welcome in the medical diagnostic field, is obviously invaluable in mass phenotyping studies that can be used in genetic research as well as for identification purposes, forensic or other.

BRIEF DESCRIPTION OF THE DRAWINGS

FIG. 1 (A to I) is an exploded view in transverse section showing two embodiments of the basic apparatus used in this invention: on the left, with a membrane and a membrane ridge, and on the right, with a gel dish and a gel temperature control plate.

FIG. 7 is a plan view of a compartmentalized tray.

FIGS. 7A and 8 are elevated transverse sections of the compartmentalized gel tray of FIG. 7 and of a gel tray without dividers, respectively.

FIG. 9 is a plan view of a snap-on tight-fitting lid for the gel trays of FIGS. 7 and 8.

FIG. 10 is a front elevation transverse section of a compartmentalized gel tray designed to receive a sliding cover.

FIG. 11 is a front elevation transverse section of a sliding cover.

FIGS. 12 and 13 show front elevation transverse sections of another type of compartmentalized gel tray and of a sliding cover adapted to it.

DETAILED DESCRIPTION OF THE INVENTION

The basic apparatus to be used with the equipment and for the processes of the present invention has been described in copending patent application Ser. No. 744,574, filed Nov. 24, 1976, now U.S. Pat. No. 4,061,561. This basic apparatus shall now be described in some detail in order that the utility and function of the improvements herein disclosed be better understood. In the following descriptions, the numbering employed in the copending application to identify the various components of the apparatus has been preserved.

The apparatus of the art shall now be described in detail, by referring to FIGS. 1A to 1F, 2, and 4, for an embodiment involving a membrane system, and to FIGS. 1A, 1B, 1E to 1I, and 3, for another embodiment involving a gel. These figures shall be discussed simultaneously in order to avoid repetition and to provide a clearer visualization of the equipment.

Figure 2:
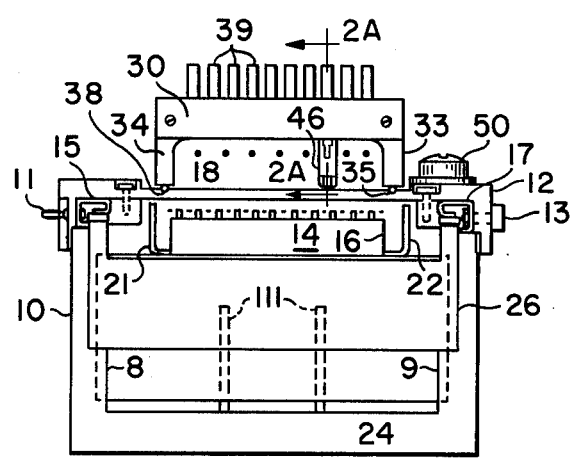
FIG. 2 is a transverse sectional view of an assembled apparatus using a membrane and a membrane bridge.

With respect to the membrane system, it will be noted that FIGS. 1 and 2 show transverse sections of the apparatus—in exploded and assembled views, respectively. while FIGS. 4A to 4D, on the other hand, give an exploded front elevation view of the same components.

Referring to these figures then it can be seen that the apparatus comprises a tank 10 which contains an electrolyte solution (now shown). Within the tank are fixed baffles (19), removable baffles (24), septum (23) and electrode frames (26, 28) which extend from slots in inner wall (8) to slots in inner wall (9). A membrane holder (14) is seated on septum (23) and two of the removable baffles (24). Channel (20) of membrane holder (14) straddles the top of septum (23). The membrane holder (14) is provided with tab grips (21, 22) and teeth (18). The teeth (18) engage perforations in a membrane (16) and keep the central portion of the membrane taut. The ends of membrane (16) are immersed in the electrolyte solution (not shown). The membrane must be made from a material that will "wick" the electrolyte solution to all areas of the membrane and keep the membrane saturated. Further, the membrane must have sufficient strength to withstand the force of the teeth when the membrane is wet. The membrane may, for example, be made from cellulose acetate, paper, or Cellogel. A cellulose acetate membrane can be kept and stored as a permanent record of the analysis. This is a very important factor in forensic science.

An applicator assembly (30) fits on to the cover (12). The applicator assembly is fitted with two feet (33, 34). The foot (34) has a registration in (38) projecting from it, and the foot (33) has a runner bar (35) projecting from it. The pin (38) and runner (35) are adapted to fit into a runner bar slot and registration pinholes on either the coverplate (12) or a sample holder, which are described in U.S. Pat. No. 4,061,561.

The cover (12) includes male and female connectors (11, 13) which make contact with the electrode wire (29) through spring interlocks (15 and 17, respectively) on the electrode frame (26). When the cover (12) is removed from the top of the tank (10), the electrical connection to the electrode wire (29) is broken by means of the spring interlocks. The electrode wire (29) is shown in detail in FIG. 1B. A platinum wire (29) is run around the slotted periphery of the electrode frame (26). The wire is connected to metal contacts (25 and 27), which complete a circuit to spring interlocks (15 and 17) shown in FIG. 2. As shown in FIG. 4D, two electrode frames (26 and 28) are placed in the tank (10) which has slots in its walls to receive the frames.

Figure 4A:
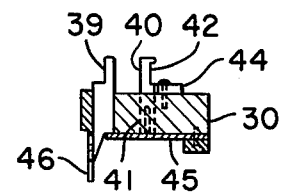
FIGS. 4A to 4D show an exploded front elevation view of the apparatus in FIG. 2 which comprises a membrane and a membrane bridge.
Figure 4B:
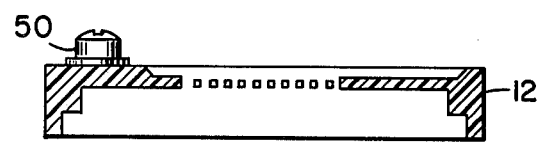
Figure 6:
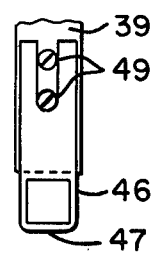
FIG. 6 is a detailed view of the applicator tip shown in FIG. 1.

Referring now to FIGS. 1F and 4A, the applicator assembly comprises a plurality of applicator buttons (39) which are adapted to hold an applicator shown in detail in FIG. 6.

The applicator buttons (39) are held in place by means of a plurality of leaf springs (45) which hold each button individually in place. A release button (40) is provided with a long arm (41) which extends across all of the parallel leaf springs (45). When the button (40) is depressed downward, all of the leaf springs are released such that all of the applicator buttons (39) are free to drop by force of gravity. The release button (40) is fitted with a groove (42), such that, when it is in the depressed position, a locking bar (44) is able to slide into the groove (42) and hold the release button in the lower position. When the applicator (30) is not in use, a protective lid (not shown) is placed over the opening in cover (12).

In FIG. 6, the applicator tip (46) is shown in more detail. The applicator tip includes a capillary opening (47) for holding the sample fluid. The applicator tip (46) is held in place by two spring-loaded split pins (49), such that the tip is easily removed.

The applicator tip (46) may be modified in length or width; for example, to vary the amount of sample held, or to cover more than one applicator position.

Figure 4C:
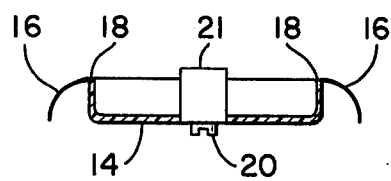
Figure 4D:
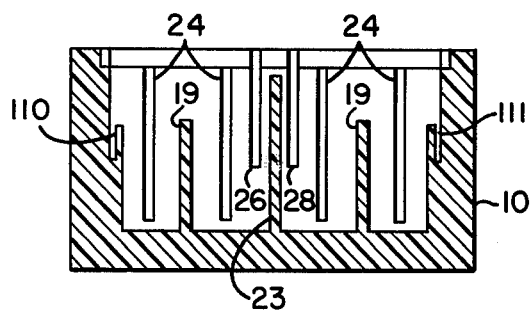
Figure 19:
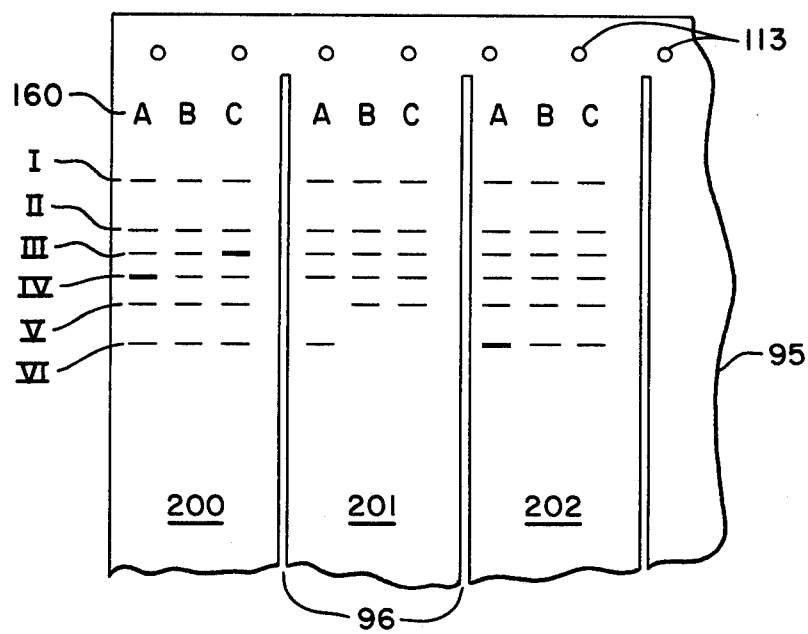
FIG. 19 shows part of a developed electrophorogram on which three protein systems have been separated in the presence of two different concentrations each of appropriate protein standards.

Referring to FIGS. 1D and 4C, the membrane holder (14) is shown in detail. The membrane holder is made of one piece of molded flexible plastic. The holder is fitted with teeth (18) and can be bent inwardly, such that the teeth (18) group corresponding perforations in a membrane (16). When released, holder (14) applies tensile force to the membrane and maintains it taut. To avoid tearing the membrane, teeth (18) are preferably semicylindrical projections or cylindrical projections, and membrane perforations (113), FIG. 19, are circular.

Figure 3:
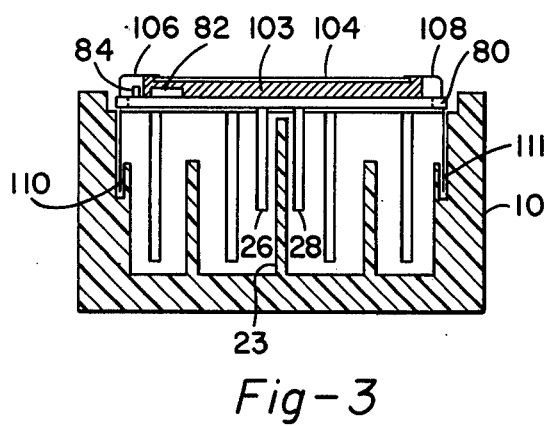
FIG. 3 is a front elevation of the tank of FIG. 1 assembled with a gel dish and a temperature control plate.

The gel electrophoretic system of the art, on the other hand, can be visualized by reference to FIGS. 1A, 1B, 1F to 1I, 3 and 5, which together show an exploded transverse section view and a front elevation view of the assembled components (FIG. 3). It can be readily seen that, in this system, membrane (16) and membrane holder (14) have been replaced by gel tray or dish (103), gel temperature control plate (80) and blotter paper strip (107).

Figure 5:
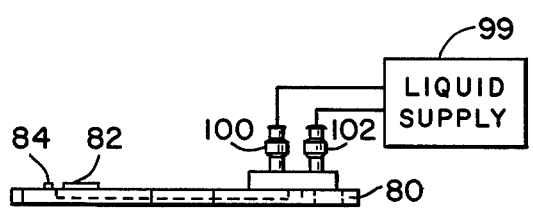
FIG. 5 is a side elevation of a temperature control plate for use with a gel tray.

Temperature control plate (80) is fitted with four retainers, two of which are shown (82, 84) from receiving and holding in place a square dish or tray (103) containing the gel material (104), such as agarose gel, that may be employed for lipoprotein separation. A temperature control liquid is circulated in the plate (80) from liquid supply (99) by means of inlet (100) and outlet (102), as shown in FIG. 5.

In FIG. 3, the temperature-control plate (80) is shown in place within the tank (10). The square tray (103) holding gel (104) is placed on plate (80) and is kept in fixed position by retainers (82, 84). Tray (103) is preferably made from a material that is an electrical insulator and a good thermal conductor. Additionally, the tray must be inert to the electrolyte. As the plate is adapted to receive a square tray, 90° rotation of the gel media is possible. Greater resoluton can be obtained by performing two migrations on the gel (104). First, the sample is pulled apart in a linear path by the electric current. The gel tray is then rotated 90° and the first migration is pulled apart from an orthogonal direction.

Contact with the electrolyte solution is made by means of wicks (106, 108) which rest on edge of the gel and pass down through wick recesses (not shown) in plate (80) and into the electrolyte solution. The tank (10) is provided with wick-retaining members (110 and 111) for receiving the lower end of each wick and holding the ends in place within the electrolyte solution. The wick-retaining members prevent the wicks from sliding off the gel and align the wicks so that they contact the gel (104) evenly across the surface. The wick alignment prevents a contact gradient from occurring. Wicks (106, 108) may be made, for example, from filter paper or plastic sponge.

During the electrophoresis process, the electric current flowing through the gel (104) causes generation of heat in the gel. The thermal convection in the gel tends to broaden the bands and cause errors due to poor resolution. This band broadening is alleviated by passing a liquid through plate (80) which has a temperature lower than the ambient temperature. For some measurements, for example, a plate temperature of 4° C has been found suitable. Blotter strips (107) made of the same material as the wicks (106, 108) and impregnated with electrolyte solution are placed along the edges of the surface of the gel (104) to facilitate electrical contact between the gel and the wicks during electrophoresis.

The remaining figures illustrate various tray and lid embodiments (FIGS. 7 to 16 and 20 to 21A) and membrane embodiments (FIGS. 17 to 19) which are the subject of the present invention and which can be used with the equipment already described to perform the diagnostic and identification processes that shall be disclosed below.

In FIG. 7, there can be seen a plan view of a novel electrophoresis tray or dish (120) which is essentially a shallow square container comprising a flat surface (128) surrounded by a peripheral wall (122). A number of parallel straight dividing ribs (121) separate the dish surface area into compartments which are permanently labelled by having one letter printed in each compartment (160). The peripheral wall may be provided with a top ridge (123) which forms a shoulder (129) for accommodating a similar peripheral ridge on a lid. The compartmentalized dish (120) just described can be seen in elevated cross-section in FIg. 7A. In FIG. 8, on the other hand, there is shown again in elevated cross-section, an embodiment of a conventional gel tray or dish (103), filled with a layer of gel (104).

Figure 14:
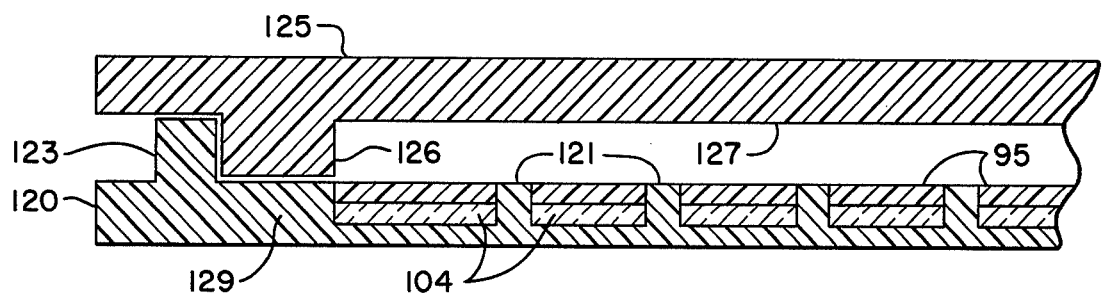
FIG. 14 is a front elevation transverse section of an assembled tray and cover pair, with the tray containing a gel over which a slotted membrane is superimposed.

FIG. 9 illustrates one type of lid for gel trays (103, 120), consisting essentially of a thin flat sheet (127) provided with a peripheral ridge (126) adapted to fit tightly within peripheral ridge (123) on shoulder (129) of gel trays (103, 120). An assembled tray and lid system is shown in FIG. 14, which comprises tray (120), lig (125), gel layer (104) and slotted membrane (95) shown in elevated cross-section. The tray and snap-on lid embodiments described in FIGS. 7 to 9 and 14 may further be provided with various conventional means for fastening the assembly more tightly and for stacking.

FIGS. 10 to 13 show further embodiments of the trays and lids of the present invention wherein either the lid (135) slides into a track formed by the walls of the tray (130), or the tray (140) slides into a track formed by the walls of the lid (145). Effective sealing of the assembled systems can be achieved in a number of ways. For example, both the tray (140) and the lid (145) can be provided wth one end wall (now shown), perpendicular to the track walls (131, 132), and at opposite ends, so that the ends of the assembly be closed. Also, flat horizontal surfaces (not shown), or shoulders, may be provided in the end wall areas of the trays which can fit closely with the lid surfaces and form additional seals.

Figure 15:
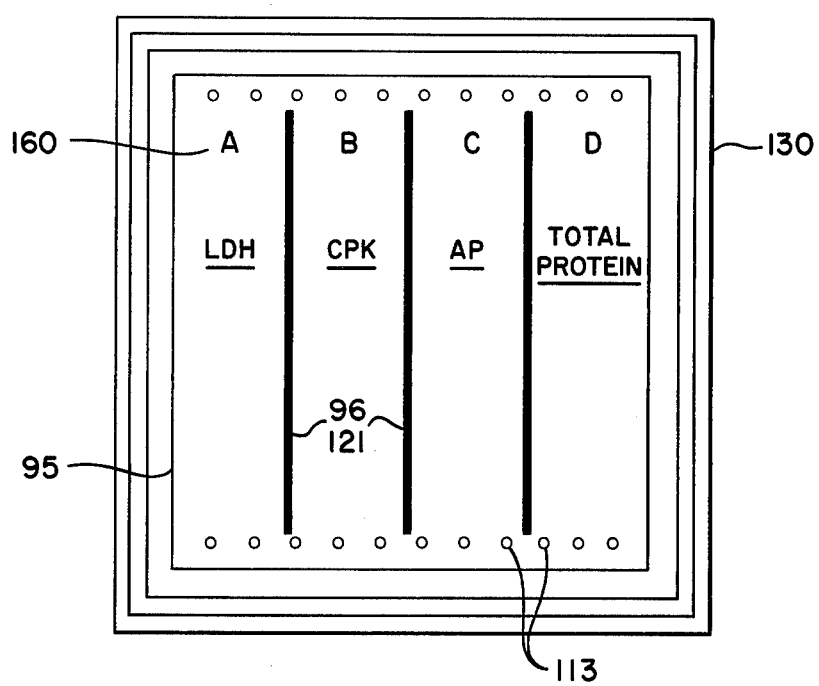
FIG. 15 is a plan view of a four-compartment dish containing a gel and a superimposed slotted membrane.
Figure 16:
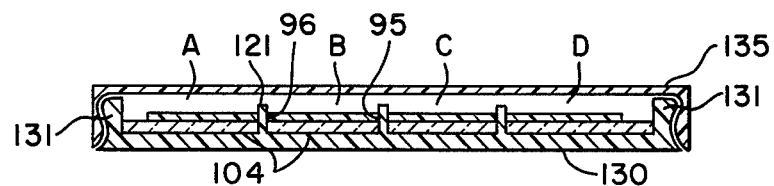
FIG. 16 is a front elevation transverse section of a dish like that of FIG. 15 assembled with a sliding cover.

FIG. 15 shows a tray in plan view which is similar to that of FIG. 14, except that the tray has only three dividing ribs (121). Circular holes (113) are designed to engage teeth (18) of membrane holder (14) shown in FIGS. 1D and 4C. In this drawing and in the elevated cross-section of the tray shown in FIG. 6, there can be seen a four-compartment tray (130) comprising three dividing ribs (121), which has been covered in FIG. 16 by sliding lid (135) between tracks (131). The compartments are filled with a gel (104) on which electrophoresis of various blood enzyme and protein systems has been run and a slotted membrane (95) comprising four strips marked by letters A, B, C, and D (160) separated by slots (96), has been superimposed upon the gel in order to contact the proteins on the gel with the enzyme substrates or color reagents with which the membrane has previously been impregnated. In this manner, a blood serum sample containing the isoenzymes of the lactic acid dehydrogenase (LDH) system has been applied to the gel (104) in compartment A of tray (130) and, after electrophoretic separation in the manner taught in U.S. Pat. No. 4,061,561, the gel has been contacted with strip A of membrane (95) previously impregnated with the tetrazolium dye and other conventional components used to develop visible electrophoretograms from this particular enzyme system. Similarly, the other compartments and strips (B, C, D) were used to detect and identify the components of different blood polymorphic enzyme or other protein systems either from the same blood sample or from samples of different origins. In this manner, as shown in the drawing of FIG. 15, creatine phosphokinase (CPK), alkaline phosphatase (AP) and total protein were run and developed simultaneously in the remaining compartments and strips (B, C, and D) respectively.

Figure 17:
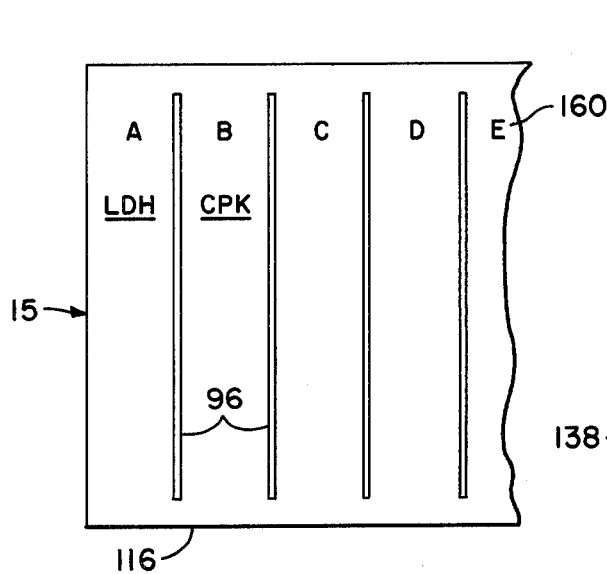
FIG. 17 is a plan view of a slotted sheet of filter paper impregnated with various developing systems for electrophoresed proteins.
Figure 18:
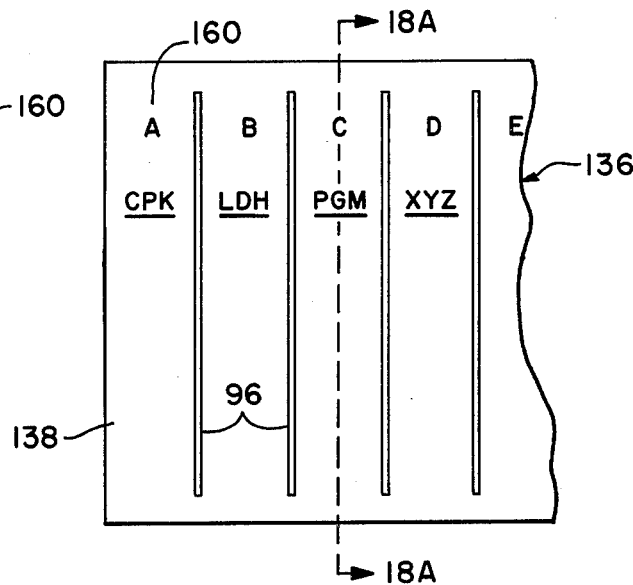
FIG. 18 is a plan view of another embodiment of the slotted sheet of FIG. 17 consisting of a polyester base coated with cellulose acetate.

FIGS. 17 and 18 show plan view of parts of two different slotted membranes preimpregnated with the substrates or other color producing agents required by the protein systems indicated on the drawings.

Thus, FIG. 17 shows five strips labelled A, B, C, D, and E (160) of a membrane (115) separated by slots (96) which extend to continous border surfaces (116). The entire membrane (115) can be made of filter paper with border areas (116) impregnated with paraffin and the strips each impregnated with the substrates or other developing reagents required by the enzyme and protein systems indicated, namely LDH(A), CPL(B), plasma protein(C), hemoglobin(D), and any other system—XYZ(E). After development, the dried membrane can be perserved as a permanent replica of the electrophoretogram.

Figure 18A:
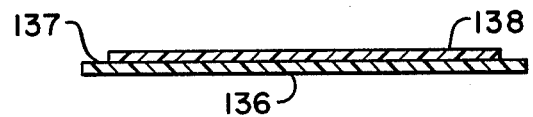
FIG. 18A shows a cross-section of the sheet of FIG. 17.

An impermeable type of membrane is shown in FIGS. 18 and 18A. Again, the membrane (136) is divided into strips by slots (96) with each cellulose acetate strip (A, B, C, D) impregnated with a particular enzyme substrate and/or color developing system as indicated, namely CPK, LDH, phosphoglucomutase (PGM), and any other system (XYZ) on strips A, B, C, and D, respectively. One feature of this particular membrane, however is that the cellulose acetate strips (138) are carried by an inert, resistant and non-porous sheet of polyester (137) such as Mylar polyester, as can be clearly seen in FIG. 18A, a cross-sectional elevation view of the membrane of FIG. 18. Other polymeric substances such as polyamides, polyimides, polyethylene, halogenated polyethylenes and the like, can be used as inert non-porous support instead of polyester, if desired.

FIG. 19 illustrates the type of pattern that may be seen on a membrane after separation and color development. Three strips (200, 201, 202) of a membrane (95) are shown, separated by slots (96). Each resulting compartment or strip has three columns labelled A, B, and C (160). On each strip has been applied a different polymorphic blood enzyme system sample which was subsequently caused to electrophoretically migrate away from the original application point, i.e., the first bar(I) below position A, to yield the bars appearing at distances II, III, IV, V, and VI. Standard preparations of the polymorphic systems are run with each unknown sample in two different concentrations (B, C) to assist in the identification and quantification of the unknown samples. In comparing the components of the unknown in column A of section 200 with its neighboring B and C columns, it becomes evident that the level IV component of the sample appears in higher concentration than normal (B, C). So does the level VI component of the sample in section 202. For the sample in 201, on the other hand, it can be seen that the level V component is missing, while a level VI component appears which is not present in the standard preparation (B, C). This then is the type of one-sheet simultaneously prepared record that can be made with the equipment and processes of this invention, identifying and quantifying up to 10 different or similar protein systems from one blood sample or from up to ten blood samples. With such profiles, the task of diagnosing several clinical conditions or identifying classes of individuals, for example, is greatly simplified due to the quantity of information which can be prepared and observed simultaneously on one electrophoretogram.

Figure 20:
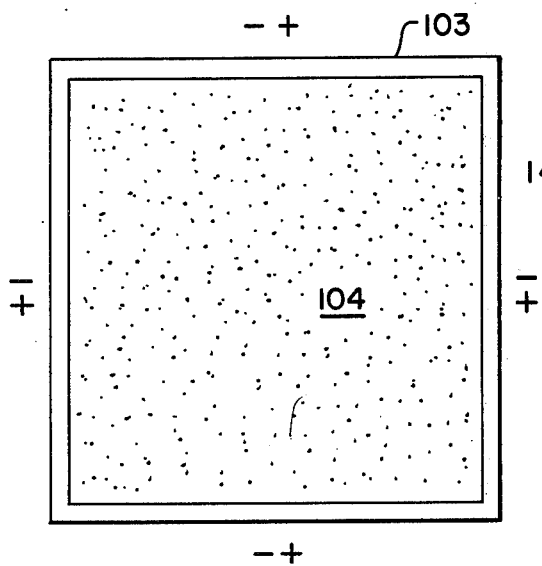
FIG. 20 is a plan view of a square tray containing precast gel mixed with ampholines for use in electrofocusing.

FIG. 20 is a top plan view of the basic square tray or dish (103) earlier disclosed, filled with a polyacrylamide gel (104) into which there are dispersed ampholines, i.e., the type of isomers of polyaminopolycarboxylic acids conventionally used for the high resolution electrofocusing process. Upon application of an electric field by means of special electrodes (not shown) placed directly on the surface of the gel, a linear pH gradient is formed and protein molecules electrophoresed in such a gradient concentrate in very narrow zones in which the net electrical charge on a given molecule is zero. In such a system, the only variable affecting the separation is the isoelectric point of a given protein. No buffer need be placed in the tank (10) of the basic apparatus (FIG. 1A). Cooling of the gel with plate 80 (FIGS. 3 and 5) is essential since a very high voltage is applied which creates a high amperage and consequently a large quantity of heat which must be dissipated instantaneously. The present apparatus allows the electrodes to be applied in any direction. Furthermore, it offers a simple easily standardized alternative to the difficult preparation of gels immediately before use, an alternative that is superior in terms of handling, transport and storage, to the flexible sheets heretofore available commercially.

Figure 21:
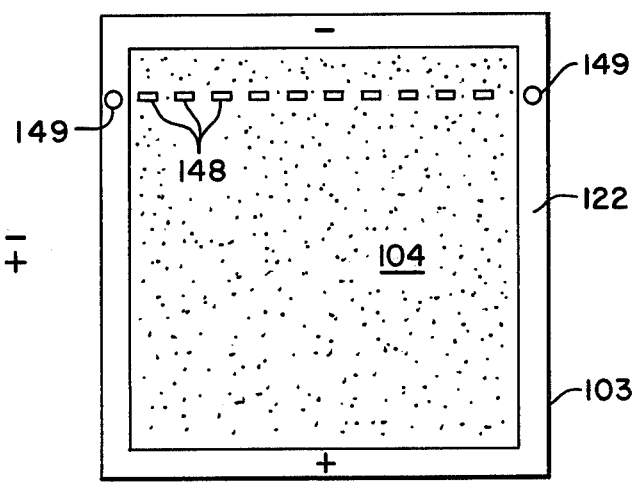
FIG. 21 is a plan view of a square tray filled with a precast gel for use in electophoresis of haptoglobin-hemoglobin complex, or other proteins.
Figure 22:
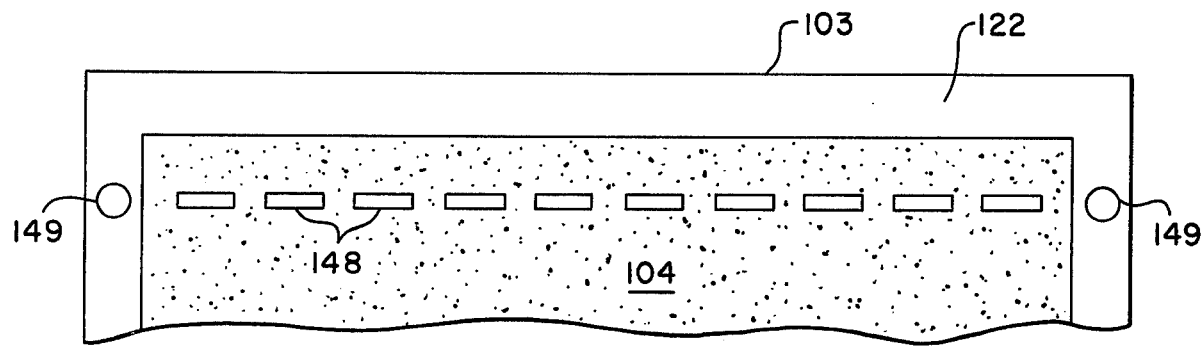
FIG. 22 is an enlargement of the area of the tray of FIG. 21 in which are located the sample-receiving cavities in the gel.
Figure 22A:
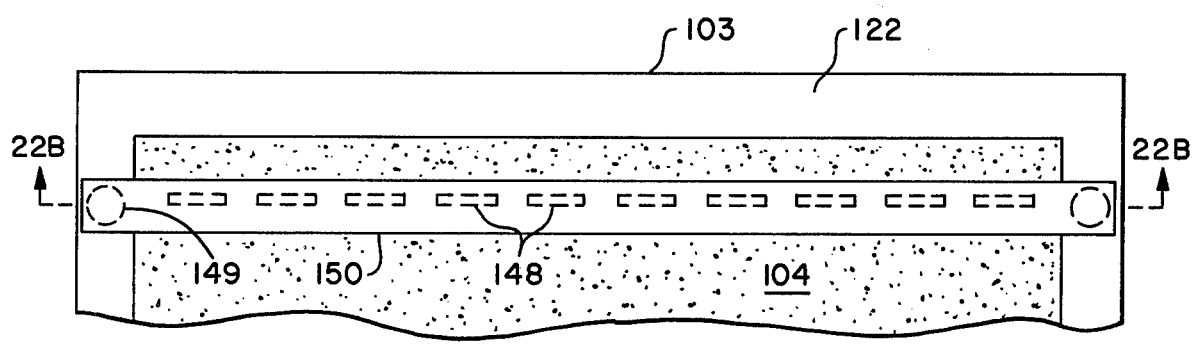
FIG. 22A shows the area of the tray illustrated in FIG. 22, but fitted with a removable and disposble plastic slot template.
Figure 22B:
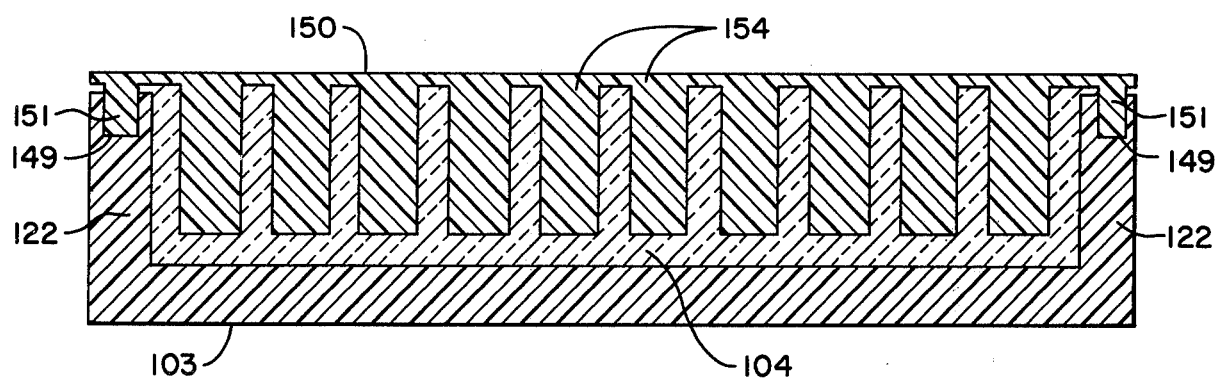
FIG. 22B is a front elevation transverse section of the tray-template assembly of FIG. 22A.

FIG. 21 is a top view of a tray (103) containing a precast gel (104) in which a line of 10 rectangular sample-receiving cavities (148) have been made. The part of the tray containing the sample-receiving cavities (148) is illustrated on a large scale in FIG. 22 in order to show sufficient detail to facilitate visualization of the tray-templates assembly shown in top view in FIG. 22A and in cross-section, in FIG. 22B.

In these figures, it can be seen that peripheral wall (122) of tray (103) is provided with two cylindrical recesses (149) designed to accept pins (151) which serve to fasten a removable and disposable plastic insert or template (150) to the tray. The template shown (150) is provided with 10 tongues (152) which serve to shape gel cavities (148) when the gel (104) is first poured into the tray (103), and to keep the cavities free of liquid between the time of fabrication and use. In other words, the tray with precast gel shown in FIG. 21 is prepared by affixing insert or template (150) to an empty tray (103) by inserting the pins (151) in recesses (149). A liquid gel making preparation is then poured into the tray to form gel (104) upon cooling, and the resulting assembly closed by a suitable cover (not shown), can be shipped or stored without deterioration until needed for electrophoresis. At that time, the plastic insert or template (150) is removed, and protein samples and standards can be placed in the gel cavities (148) for electrophoresis. The type of tray just described is used mainly for the genetic typing of polymorphic proteins such as those from the haptoglobin-hemoglobin complex, but can be used for the separation of many protein mixtures requiring the relatively high resolution medium of acrylamide gel. The polyacrylamide gel in the tray can have either a fixed concentration of polymer throughout, or the concentration may vary to produce either a linear gradient or a step gradient. The polyacrylamide molecules act as a mechanical sieve, aiding both separation and resolution.

Figure 23:
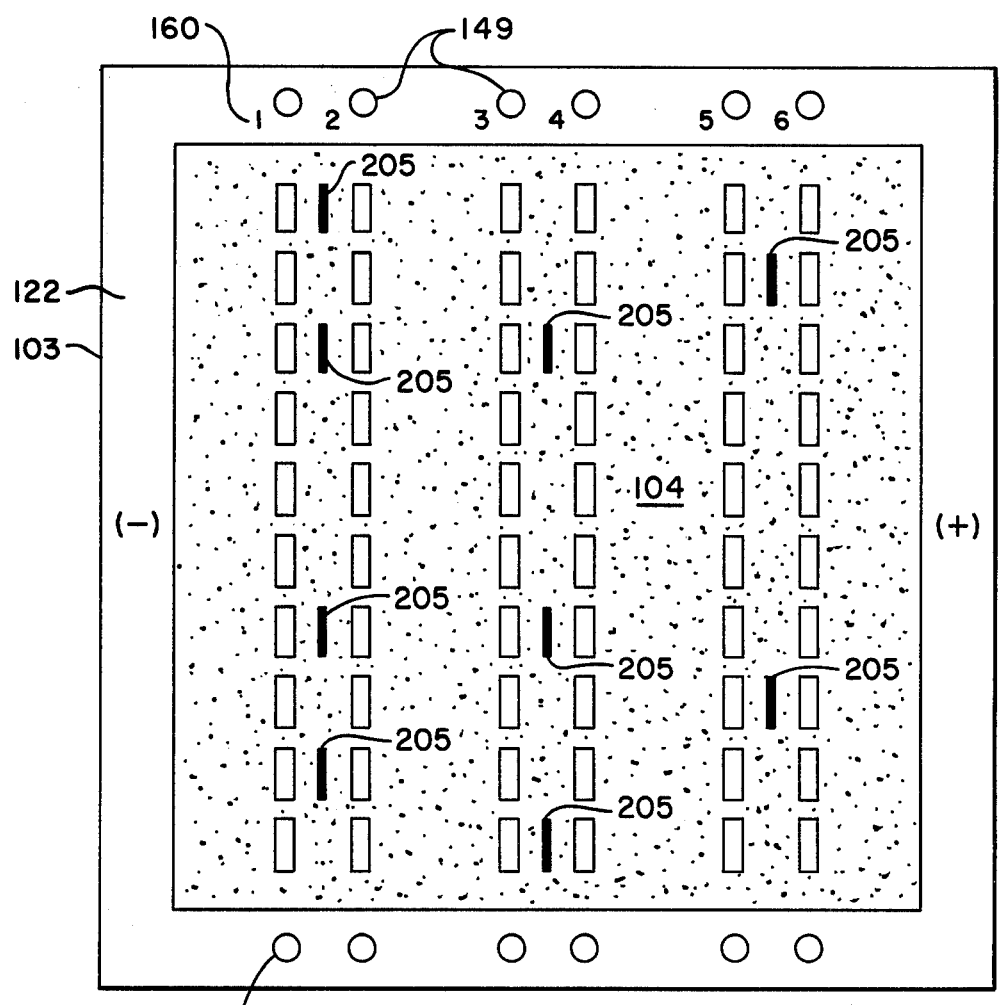
FIG. 23 is a plan view of a tray with precast gel, designed for cross-over electrophoresis.

FIG. 23 shows a square tray with precast gel designed to employ specific antisera in cross-over electrophoresis for the analysis of Australian antigen (infectious hepatitis), syphilis, and other infectious diseases. The tray and the method can also be applied to species identification in the investigation of fresh or dried blood or other physiological fluids. As can be seen from the drawings, the precast gel tray (103) is basically similar to that of FIG. 21, except that the gel sheet (104) is provided with three pairs of lines of 10 cavities (148) each, said lines being labelled 1, 2, 3, 4, 5, and 6 (160). The trays are prepared in the same manner as that of FIG. 21, except of course that six plastic templates are used instead of the single one (150) employed for the tray of FIGS. 21 to 22B. The template pins (151, FIGS. 22A and 22B) snap into cylindrical recesses (149) and the tray is then filled with gel (104) as earlier described. Before use, the templates are removed, leaving open cavities (148) for receiving antigen and antiserum samples. The gel cavities are used in pairs, with the antigen sample being placed in the cavity located on the electrically negative side of the pair (rows 1, 3, and 5), as indicated by the minus sign (−) printed on the lefthand portion of the tray's peripheral wall (122), while the specific antiserum sample is placed in the cavity located in the positive side of the pair (rows 2, 4, and 6). When voltage is applied to the up to 30 samples in the tray, the antigen and antiserum proteins migrate toward each other and react upon crossing-over or meeting to create a visible line of precipitin. Nine such lines (205) can be seen in the drawing, having formed between certain pairs only. The absence of a precipitin line between a pair of cavities indicates the absence of the specific antigen in the sample that was placed in the lefthand cavity of that pair.

It should be noted that in the preparation of the various precast gel trays and membrane described so far, it is possible to delay addition of any unstable substrate and reagents to the precast gel or membrane until the moment of use. In the case of membrane, however, some of the unstable ingredients may be safely incorporated at the time of membrane manufacture by resorting to the technique of freeze drying.

A better realization of the possibilities of the equipment and processes of the present invention may be obtained by reference to the medical, genetic and forensic literature for review of the polymorphic protein systems already mentioned and assessment of the information that they can reveal.

What is claimed is:

1. A microelectrophoretic process for the simultaneous separation and identification of the components of two or more protein systems, comprising:
   (a) applying an unknown protein sample of a protein system different in nature or in origin and a standard protein sample for the system selected to each compartment of a shallow rib-divided tray containing a suitable gel;
   (b) subjecting the samples so applied to electrophoresis;
   (c) overlaying upon the sample-carrying gel in the tray a membrane divided into strips by slots so placed that they accept the dividing ribs of the tray in a manner such that close contact is established and maintained between the surface of the gel and the surface of the membrane;
   (d) allowing the proteins distributed on the gel to react with suitable specific substrates and color-forming reagents preimpregnated on each strip of the membrane in an arrangement corresponding to that of the protein systems located in the individual compartments of the gel; and
   (e) removing and drying the membrane to produce a composite electrophoretogram.

2. The process of claim 1 wherein the electrophoresis is carried out on the slotted membrane and the specific substrates and color-forming reagents are in the gel.

3. The process of claim 1 wherein the gel compartments carry identical protein systems of different origin and the membrane is impregnated with the one substrate and color-forming reagent combination required by said system.

4. The process of claim 1 wherein at least two protein systems determined are selected from the group of polymorphic enzyme systems consisting of lactic acid dehydrogenase, alkaline phosphatase and creatine phosphokinase.

5. The process of claim 4 wherein at least one additional protein system is determined, said system being selected from the group consisting of hemoglobin and total blood protein.

6. The process of claim 5 wherein additional polymorphic protein systems are determined to fill all the compartments of a 10-compartment tray, said additional system being selected from the group consisting of phosphoglucomutase, erythrocyte acid phosphatase, glucose-6-phosphate dehydrogenase, adenylate kinase, esterase D and adenosine deaminase.

7. As an article of manufacture, a cellulose acetate membrane divided into at least two strips by at least one slot, each strip having been impregnated with a substrate and color-forming reagent specific to one polymorphic protein system from the group consisting of lactic acid dehydrogenase (LDH), alkaline phosphatase (AP), creatine phosphokinase (CPK), erythrocyte acid phosphatase (EAP), glucose-6-phosphate dehydrogenase (G-6PD), adenylate kinase (AK), group specific component (Gc), lipoprotein (lp), adenosine deaminase (ADA), 6-phosphogluconate dehydrogenase (6-PGD), glutamic pyruvic transaminase (GPT), esterase D (EsD) and others.

8. As an article of manufacture, a shallow gel-containing tray divided into at least two compartments by one dividing rib, each compartment having been impregnated with a substrate and color-forming reagent specific to one of the polymorphic protein systems listed in claim 7.

9. The slotted membrane of claim 7 consisting of a polyester base layer coated with cellulose acetate in the reagent-containing strip areas.

10. As an article of manufacture, a shallow square gel-containing tray fitted with a tight-closing cover, which can be used in suitable microelectrophoretic apparatus for the simultaneous determination of up to thirty protein samples by electrophoresis.

11. The tray and cover system of claim 10 designed to join in a sliding arrangement.

12. The tray and cover assembly of claim 10 containing up to 30 pairs of sample-receiving slots in the gel, said pairs being arranged to achieve the cross-over migration of antigen and antiserum, and the resulting formation of visible precipitins.

13. As an article of manufacture, the gel-filled tray and cover of claim 10, with the tray being divided in up to ten compartments by parallel ribs.

14. The tray and cover assembly of claim 10 wherein the gel contains ampholines of the types used in electrofocusing.

* * * * *